United States Patent
Doi et al.

(10) Patent No.: US 7,547,552 B2
(45) Date of Patent: Jun. 16, 2009

(54) INDICATION COMPOSITION FOR SURGICAL INSTRUMENT CLEANING EVALUATION

(75) Inventors: Mikio Doi, Suita (JP); Shigeru Ura, Kitakatsuragi-gun (JP)

(73) Assignee: AMTEC Co., Ltd., Osaka-shi (JP)

( * ) Notice: Subject to any disclaimer, the term of this patent is extended or adjusted under 35 U.S.C. 154(b) by 143 days.

(21) Appl. No.: 11/632,739

(22) PCT Filed: May 8, 2006

(86) PCT No.: PCT/JP2006/009261
§ 371 (c)(1), (2), (4) Date: Feb. 22, 2007

(87) PCT Pub. No.: WO2007/004353
PCT Pub. Date: Jan. 11, 2007

(65) Prior Publication Data
US 2007/0249054 A1 Oct. 25, 2007

(30) Foreign Application Priority Data
Jun. 30, 2005 (JP) ............................... 2005-192476

(51) Int. Cl.
G01N 31/22 (2006.01)
G01N 21/77 (2006.01)

(52) U.S. Cl. ............................... 436/15; 436/8; 436/66; 436/86; 436/88; 436/164; 436/166; 422/55; 422/57; 422/61; 252/408.1

(58) Field of Classification Search ............... 436/8, 436/15, 63, 66, 71, 86, 88, 164, 166, 169, 436/174; 422/55, 56, 57, 58, 61, 82.05; 252/408.1
See application file for complete search history.

(56) References Cited

U.S. PATENT DOCUMENTS

| | | | | |
|---|---|---|---|---|
| 5,498,421 | A * | 3/1996 | Grinstaff et al. | 424/450 |
| 6,066,325 | A * | 5/2000 | Wallace et al. | 424/400 |
| 6,107,097 | A * | 8/2000 | Pfeifer | 436/69 |
| 6,394,111 | B1 * | 5/2002 | Jacobs et al. | 134/113 |
| 6,447,990 | B1 * | 9/2002 | Alfa | 435/4 |
| 6,475,434 | B1 * | 11/2002 | Darouiche | 422/28 |
| 6,653,146 | B1 * | 11/2003 | Ruvinsky et al. | 436/172 |
| 7,001,773 | B2 * | 2/2006 | Lepow et al. | 436/8 |
| 2003/0109406 | A1 * | 6/2003 | Cooney | 510/392 |

FOREIGN PATENT DOCUMENTS

| | | | |
|---|---|---|---|
| JP | 08-043272 | | 2/1996 |
| JP | 2000-051796 | | 2/2000 |
| JP | 2001-031999 | | 2/2001 |
| WO | 97/27482 | | 7/1997 |
| WO | 2007/81004 | * | 7/2007 |

OTHER PUBLICATIONS

Fushimi, Ryo et al., "Problems of Cleaning caused by Contaminated Objects after Disinfection", vol. 73, No. 6, pp. 281-289, 2003. (with English abstract).

* cited by examiner

Primary Examiner—Maureen M Wallenhorst
(74) Attorney, Agent, or Firm—Oblon, Spivak, McClelland, Maier & Neustadt, P.C.

(57) ABSTRACT

The present invention provides an indicator composition for evaluating cleaning of a medical instrument that includes an extracellular matrix component and hemoglobin, as a contamination model having cleaning profile resembling an actual contaminant adhered to a medical instrument such as a surgical instrument.

12 Claims, 3 Drawing Sheets

(a)

(b)

(a) (b)

| Extra-cellular Matrix Content | Immersion Time (min.) | | | | | |
|---|---|---|---|---|---|---|
| | 0 | 5 | 15 | 25 | 35 | 45 |
| 1% | | | | | | |
| 5% | | | | | | |
| 10% | | | | | | |
| 20% | | | | | | |

Figure 2

INDICATION COMPOSITION FOR SURGICAL INSTRUMENT CLEANING EVALUATION

TECHNICAL FIELD

The present invention relates to an indicator composition for evaluating cleaning of a medical instrument contaminated with body fluid or blood during, for example, surgery; to an indicator device for evaluating cleaning of a medical instrument utilizing such an indicator composition; to a method for evaluating cleaning of a medical instrument wherein such an indicator device is used; and to a kit for evaluating cleaning of a medical instrument comprising a combination of such a cleaning evaluation indicator device used in the above method and a color reagent.

BACKGROUND ART

With the advance in medical technology, medical apparatuses having complicated shapes and medical instruments made of special materials are widely used. Therefore, there is a need for a method for cleaning, disinfecting, and sterilizing these medical devices and instruments safely and reliably.

In particular, the quality of cleaning greatly affects subsequent disinfection and sterilization processes, and therefore a method for evaluating the quality of cleaning is of importance.

In recent years, there is demand for establishment of a cleaning evaluation method in medical fields, and standards for evaluation of cleaning draws international attention.

An indirect evaluation method, one of cleaning evaluation methods, is a method in which a contamination model closely resembling actual contaminants is used for evaluation. The contamination model is subjected to a cleaning process to be evaluated, and the degree of cleaning of contaminated medical instruments is evaluated based on how much the contamination model is remained.

As a conventionally used contamination models, there is a model containing a mixture of egg yolk, dye, mucin, and the like (see, for example, "209 points of Cleaning, Disinfection, and Sterilization", The Japanese Journal of Infection Control 2004 Supplement, p. 55, Medicus SHUPPAN (Japan), Nov. 15, 2004, a non-patent document).

As another contamination model, there is a model obtained by sticking hemoglobin, a major component of blood, and albumin on a stainless steel plate with the use of fibrin (see, for example, International Publication No. WO97/27482).

However, the contamination model described in the above non-patent document contains almost no blood or body tissue components, which are main contaminants, and is therefore apparently different from contamination with blood and tissue components. Thus, this contamination model has a problem of not being able to properly evaluate a cleaning process for a surgical instrument, or the like, contaminated with blood and tissue.

The contamination model described in WO97/27482 contains only blood components, which are easily removed with, for example, an alkali detergent. However, actual main contaminants during surgery contain both blood and tissue components, and are therefore difficult to be removed. Thus, this contamination model also has a problem of not being able to properly evaluate a cleaning process of actual contaminants, which is difficult to be removed.

DISCLOSURE OF THE INVENTION

The present invention was made in view of the above problems, and an object of the present invention is to provide a contamination model which behaves more like actual contaminants adhered to a medical instrument during, for example, surgery than do conventional contamination models, and the degree of difficulty in cleaning of which is capable of being adjusted appropriately.

As a result of the effort to achieve the above object, the present inventors have found that a composition comprising an extracellular matrix component and hemoglobin behaves, in a cleaning process, closely like patient's blood and tissue components adhered to a medical instrument during, for example, surgery, and have completed the present invention.

An indicator composition for evaluating cleaning of a medical instrument (hereinafter, also simply referred to as an "indicator composition") according to the present invention comprises an extracellular matrix component and hemoglobin.

According to the indicator composition of the present invention, it is possible to properly evaluate the degree of cleaning of a medical instrument to which contaminants due to blood and tissue components have adhered.

According to the indicator composition of the present invention, it is also possible to adjust the degree of difficulty in cleaning of the indicator composition to that corresponding to the contamination level of a medical instrument to be cleaned, by varying the concentration of the extracellular matrix component in the composition, and/or treating the composition with a disinfecting agent to denature the proteins therein.

BRIEF DESCRIPTION OF DRAWINGS

FIG. 2 is a set of photographs which show the amount of indicator compositions remained after cleaning for various time periods on indicator devices to which the indicator compositions, each having a different concentration of the extracellular matrix component, had been applied.

BEST MODE FOR CARRYING OUT THE INVENTION

Figure 1:
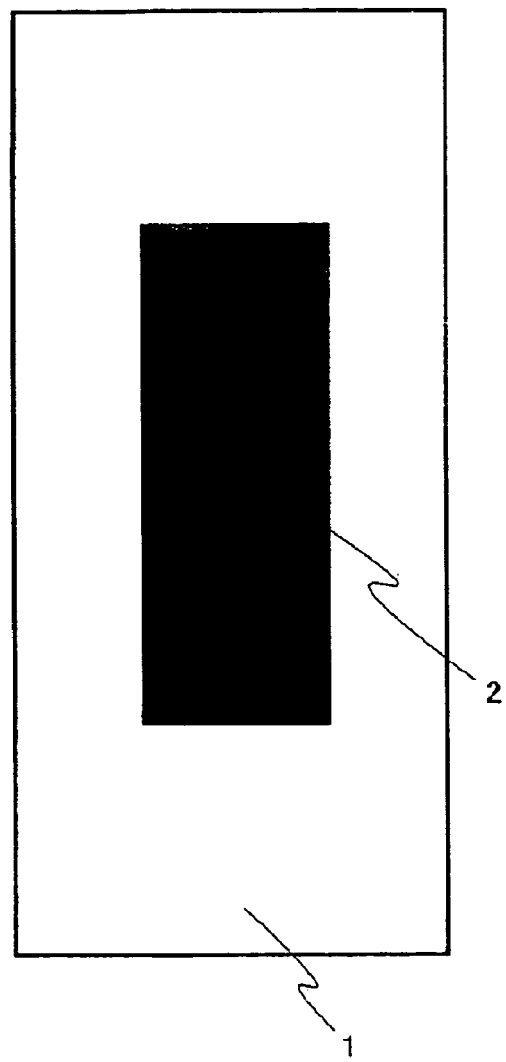
FIG. 1 shows a cleaning evaluation indicator device, obtained in Example 1 of the present invention, in a plane view (a) and in a schematic cross-sectional view (b). 1: test substrate; 2: indicator composition.
Figure 1:
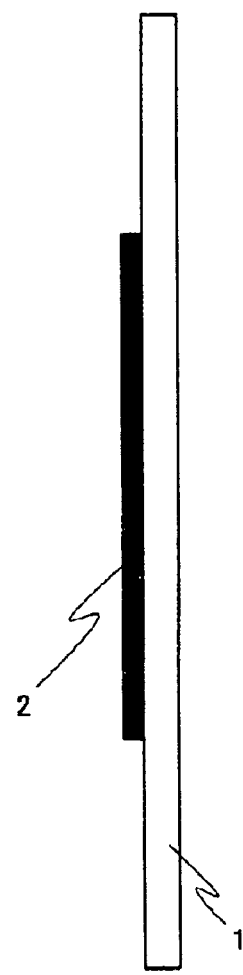

The present invention will be described hereinafter with reference to an embodiment, but is not limited thereto.

A first object of the present invention is to provide an indicator composition comprising an extracellular matrix component and hemoglobin.

The extracellular matrix component contained in the indicator composition of the present invention is composed of extracellular substances, mainly fibrous proteins, proteoglycans, and cell-adhesive proteins, which are contiguously present from the outside vicinity of animal cell membranes toward outside and form a network structure.

Fibrous proteins constituting the extracellular matrix component include collagen, elastin, and the like. A proteoglycan constituting the extracellular matrix component comprises core protein and glycosaminoglycan. Cell-adhesive proteins constituting the extracellular matrix component include fibronectin, laminin, tenascin and the like.

Substances constituting the extracellular matrix component contained in the indicator composition of the present invention are not particularly limited. It is preferable that the indicator composition of the present invention comprises at least collagen and proteoglycan. The degree of difficulty in cleaning of such an indicator composition can be adjusted by changing their concentrations.

The extracellular matrix component is obtainable from various tissues of an animal such as chicken, pig, cow, horse, and mouse. It is particularly preferable that the extracellular matrix component is obtained from chicken cartilage. Chicken cartilage is available with ease and at a low cost.

Specifically, the extracellular matrix component can be obtained as an aqueous suspension by homogenizing small cut pieces of chicken cartilage with a mixer, filtering the homogenate through stainless steel mesh or mesh cloth (e.g., 12 mesh), diluting the filtrate appropriately with water, and again filtering the diluted suspension through mesh cloth (e.g., 100 mesh).

Hemoglobin contained in the indicator composition of the present invention is a chromoprotein present in erythrocytes, and is composed of heme and globin. Hemoglobin can be appropriately obtained from an animal such as chicken, pig, cow, horse, and mouse using a routine method. Alternatively, a commercially-available product may be used.

In preparing the indicator composition of the present invention, preferably, the extracellular matrix component is used as a 0.1 to 50 wt % aqueous suspension and hemoglobin is used as a 1 to 10 wt % aqueous suspension. The thus prepared indicator composition provides a contamination model closely resembling actual contaminants, that is, improves the quality of contamination model product.

The composition ratio between the extracellular matrix component and hemoglobin constituting the indicator composition of the present invention is not particularly limited. In general, the appropriate amount of hemoglobin contained in an aqueous suspension is in the range of about 0.1 to 10 parts by weight per 1 part by weight of the extracellular matrix component contained in the aqueous suspension.

The indicator composition of the present invention may further contain, in addition to the extracellular matrix component and hemoglobin described above, a serum protein such as albumin or globulin. In particular, albumin is preferably used as a serum protein.

If the indicator composition of the present invention contains a serum protein, the amount of the serum protein is appropriately in the range of about 1 to 10% by weight, based on the total weight of the indicator composition.

The indicator composition of the present invention may further contain myoglobin. If the indicator composition contains myoglobin, the amount of myoglobin is appropriately in the range of about 1 to 10% by weight, based on the total weight of the indicator composition.

The indicator composition of the present invention may further contain myosin, myosin filament, actin and/or actin filament. If the indicator composition contains one or more of these substances, the amount of the one or more substances is appropriately in the range of about 1 to 10% by weight, based on the total weight of the indicator composition.

The indicator composition of the present invention may further contain a lipid such as glyceride, wax, sterol ester, phospholipid, or glycolipid. If the indicator composition of the present invention contains such a lipid, the amount of the lipid is appropriately in the range of about 0.1 to 10% by weight, based on the total weight of the indicator composition.

The indicator composition of the present invention may further contain a fatty acid, a higher alcohol, and/or a hydrocarbon.

It is preferable that the indicator composition of the present invention contains, in addition to the extracellular matrix component and hemoglobin, a substance selected from the group consisting of serum proteins, myoglobin, myosin, myosin filament, actin, actin filament, and lipids. Such an indicator composition is a contamination model more closely resembling actual contaminants.

The indicator composition of the present invention can be produced by conventional mixing of an aqueous solution or suspension of the extracellular matrix component, an aqueous solution or suspension of hemoglobin, and, if desired, an aqueous solution or suspension of the optional component mentioned above. It should be noted that as a matter of course, the indicator composition of the present invention does not include a composition which contains only components obtained from the same individual or is directly available from a naturally occurring product.

For long-term storage, the indicator composition of the present invention can be, for example, lyophilized. Such a lyophilized indicator composition can be re-suspended into distilled water or physiological saline before use.

A second object of the present invention is to provide an indicator device for evaluating cleaning of a medical instrument, obtained by attaching the above-described medical instrument cleaning evaluation indicator composition to a test substrate (solid support) and then solidifying the indicator composition.

The material of the test substrate is preferably the same as that of a medical instrument or the like. Specific examples of the material of the test substrate include: metals such as stainless steel, aluminum, copper, brass, and titanium; glass; and resins such as polyethylene, polypropylene, silicone resins, polyvinyl chloride, Teflon®, polycarbonate, polyester, polymethacrylate, polystyrene, ABS, nylon, acetal resins, acrylic resins, fluorocarbon resins, methylenepentene resins, polyurethane, phenol resins, melamine resins, and epoxy resins. In particular, stainless steel and silicone resins are preferred.

Preferably, the surface structure of the test substrate is the same as or closely similar to that of a medical instrument or the like. Preferably, the shape of the test substrate is closely similar to the shape of part of a medical instrument, which part is difficult to be cleaned (e.g., a box lock part or gripping part of a forceps, or a forceps in an endoscope). The test substrate may be in, for example, a plate-like, disc-like, rod-like, or hollow tube-like shape.

The surface roughness of the test substrate may be varied by, for example, grinding its surface with an abrasive of grain size No. 150 to 180 defined in Japanese Industrial Standards so as to adjust the degree of difficulty in cleaning. The surface of the test substrate may be treated so as to adjust the hydrophilicity or hydrophobicity.

The dimensions of the test substrate are not particularly limited. The dimensions of about 0.5 to 3 cm long by about 5 to 10 cm wide and about 0.1 to 10 mm thick are enough for a test substrate in a quadrangular plate-like shape.

Any conventional method can be used for attaching the indicator composition of the present invention to a test substrate. Conveniently, the indicator composition in liquid form can be applied directly onto a test substrate. The applied amount is not particularly limited, but is preferably in the range of about 1 to 50 mg per 1 $cm^2$ of the test substrate.

The applied indicator composition is then solidified. Conveniently, it is solidified by drying. The temperature and time for drying are not particularly limited. For example, about 1 to 24 hours is enough for drying at room temperature, and about 1 to 2 hours is enough for drying at 40° C.

Two or more indicator compositions, the degrees of difficulty in cleaning of which are different, may be stuck to a single surface of a test substrate.

If a test substrate has two or more surfaces, two indicator compositions having different degrees of difficulty in cleaning may be stuck to two different surfaces respectively (e.g., front and back surfaces of a plate-like test substrate).

If the indicator composition attached to the indicator device of the present invention is treated by, for example, immersion in a disinfectant so as to denature proteins contained in the indicator composition, the denatured proteins behave as substances more difficult to be removed than undenatured proteins.

The indicator composition of the present invention treated with a disinfectant can be used as a contamination model more closely resembling a contaminated medical instrument which has been treated with a disinfectant before cleaning so that the adhered contaminants have become harder to be removed.

Examples of a disinfectant for such a purpose as described above include sodium hypochlorite, povidone iodine, benzalkonium chloride, benzethonium chloride, chlorhexidine gluconate, alkyldiaminoethylglycine chloride, alkylpolyaminoethylglycine hydrochloride, glutaral, phtharal, peracetic acid, ethanol, isopropanol, formalin, cresol and soap solution, acrinol, oxydol, Hibitane® alcohol, Iodine Tincture™, Isodine®, Hibitane®, Rivanol™, and the like.

A third object of the present invention is to provide a method for evaluating cleaning of a contaminated medical instrument.

The cleaning evaluation method can be carried out by, for example, cleaning the above-described medical instrument cleaning evaluation indicator device together with a contaminated medical instrument to be cleaned in practice, and detecting the indicator composition remaining on the indicator device to determine the degree of cleaning of the medical instrument.

The cleaning evaluation method may be carried out by, for example, cleaning medical instrument cleaning evaluation indicator devices under predetermined cleaning conditions, and detecting the residual degree of the indicator composition remaining on the indicator devices after, for example, predetermined time periods of cleaning, and based on the results, setting conditions for cleaning a medical instrument.

The cleaning evaluation method may be carried out by, for example, cleaning the medical instrument cleaning evaluation indicator device of the present invention under the same cleaning conditions as those of a cleaning process for a contaminated medical instrument, and detecting the indicator composition remaining on the indicator device at intervals of, for example, 10 minutes to determine the required cleaning time as a function of the degree of difficulty in cleaning under the cleaning process, and based on the results, setting an appropriate time required for cleaning a contaminated medical instrument under the cleaning process.

The cleaning evaluation method can be used for checking whether a predetermined cleaning process works properly, and carried out by, for example, cleaning the medical instrument cleaning evaluation indicator device of the present invention under the predetermined cleaning conditions, prior to daily cleaning of medical instruments, and observing whether the residual degree of the indicator composition remaining on the indicator device after a predetermined time period of cleaning is the same as usual, that is, the contamination model is removed at the same level as usual.

The cleaning evaluation method can also be used for checking whether cleaning conditions are normal, and carried out by, for example, cleaning the medical instrument cleaning evaluation indicator device of the present invention together with a contaminated medical instrument to be cleaned in practice, and observing whether the residual degree of the indicator composition remaining on the indicator device is the same as usual.

A cleaning agent per se and a cleaning process per se used for the above cleaning are those conventionally used for cleaning a medical instrument.

Depending on the purpose of use of the present inventions as described above, the medical instrument cleaning evaluation indicator device of the present invention as described above is paced in a cleaning device together with a contaminated medical instrument to be cleaned and both are cleaned at the same time, or alternatively the medical instrument cleaning evaluation indicator device of the present invention is placed and cleaned alone in a cleaning device.

If the indicator device(s) to which two or more cleaning evaluation indicator compositions with different degrees of difficulty in cleaning have been stuck are placed in a cleaning device, it is possible to determine the degree of cleaning of a contaminated medical instrument with higher accuracy.

In the case where the indicator composition contains a colored component such as hemoglobin so that the residual indicator composition can be visually recognized, one may detect the presence or absence of the indicator composition remaining on the indicator device in the course of, or after the completion of, a cleaning process by macroscopically checking the degree of the residual indicator composition.

In the case of requiring more accurate determination, it is preferable to use color reaction of a substance constituting the indicator composition.

Such a determination method can be carried out using any routine method depending on a substance to be detected. If a substance to be detected is protein, the determination is carried out by means of, for example, Kjeldahl reaction, Lowry reaction, Millon reaction, ninhydrin reaction, Pauly reaction, xanthoprotein reaction, biuret reaction, or the like. If a substance to be detected is glycoconjugate, the determination is carried out by means of, for example, PAS reaction, mucicarmine stain, alcian blue stain, colloidal iron stain, toluidine blue stain, Best's carmine stain, or the like. If a substance to be detected is lipid, the determination is carried out by means of, for example, Sudan III stain, Oil red O stain, Sudan black B stain, Nile blue stain, or the like.

Since the indicator composition of the present invention contains a protein, ninhydrin reaction widely used for detecting a protein is particularly preferred.

A fourth object of the present invention is to provide a kit for evaluating cleaning of a medical instrument comprising a combination of the medical instrument cleaning evaluation indicator device to be used in the medical instrument cleaning evaluation method as described above and a color reagent.

Such a kit preferably comprises a combination of an indicator device(s), to which two or more medical instrument cleaning evaluation indicator compositions according to the present invention with different degrees of difficulty in cleaning, for example, corresponding to those of contaminants due to surgery or the like have been attached, and a color reagent suitable for color reaction of a contaminant presumed to adhere to a medical instrument due to a surgical site. Such a kit may comprise a combination of the most standard cleaning evaluation indicator device and a color reagent for, e.g., ninhydrin reaction.

The present invention will be described below with reference to the following Example and Experiment. However, the present invention is not limited to the Example and Experiment.

EXAMPLE 1

(1) Preparation of Indicator Compositions

Chicken cartilage (100 g) was cut into about 10 mm cubic pieces, and was then homogenized with a mixer. The homogenate was filtered through stainless steel mesh (12 mesh). After adding water (40 mL), the filtrate was further filtered through mesh cloth (100 mesh) to prepare a 50% aqueous suspension of extracellular matrix component.

Hemoglobin (100 mg, bovine hemoglobin; Tokyo Chemical Industry Co., Ltd., JAPAN) and albumin (60 mg, bovine serum albumin; Nacalai tesque, JAPAN) were dissolved in distilled water (1.8 g). The thus obtained solution was added to the above 50% aqueous suspension of extracellular matrix component (40 mg) to prepare the indicator composition (2 g).

The indicator composition contained 1% by weight of extracellular matrix component comprising collagen and proteoglycan, 5% by weight of hemoglobin, and 3% by weight of albumin.

Similarly, indicator compositions, each having a different concentration of the extracellular matrix component (5 wt %, 10 wt %, and 20 wt %), were prepared.

(2) Preparation of Indicator Devices

Each of the thus obtained indicator compositions (70 μL) was applied onto a surface of a separate stainless steel plate (50 mm×15 mm×0.1 mm), and dried at room temperature (25° C.) for 1 hour. The stainless steel plates were subjected to a 3-minute immersion in each of a 10% sodium hypochlorite solution, a 6% peracetic acid solution, an 80% ethanol solution, and a 70% isopropanol solution, and dried at room temperature for 1 hour to obtain cleaning evaluation indicator devices. The plan view and the schematic cross-sectional view of one of the indicator devices are shown in FIGS. 1A and B, respectively.

Experiment 1

(1) Preparation of Pseudo-Contaminated Medical Instruments

In order to simulate contaminated medical instruments, stainless steel plates (50 mm×15 mm×0.1 mm each) were pressed on chopped pig meat (50 g) containing skin tissue, connective tissue, and muscular tissue so as to attach pig tissue components on the plates. Bovine blood (70 μl) was then added onto the surfaces to which pig tissue components had been attached, and then the surfaces were dried at 40° C. for 1 hour to prepare pseudo medical instruments contaminated.

(2) Cleaning

A cleaning agent (60 mL of Biotect® 66; Kao Corporation, JAPAN) was dissolved in water (5,940 ml) to prepare a cleaning solution. The cleaning evaluation indicator devices obtained in the Example 1 and the pseudo-contaminated medical instruments were immersed in the cleaning solution at 37° C. for 5 min, 15 min, 25 min, 35 min, or 45 min.

(3) Detection of Residual Contaminant

An analytical reagent for ninhydrin reaction was prepared by adding distilled water (100 mL) to a solution of ninhydrin (200 mg) dissolved in ethanol (1 mL). The test samples obtained after subjecting to the cleaning process described above were stained with the analytical reagent. The results are shown in FIG. 2.

The removal rates (wt %) of contamination model on test samples were calculated from the dry weights measured before and after predetermined time periods of cleaning. The results are shown in FIG. 3.

Figure 3:
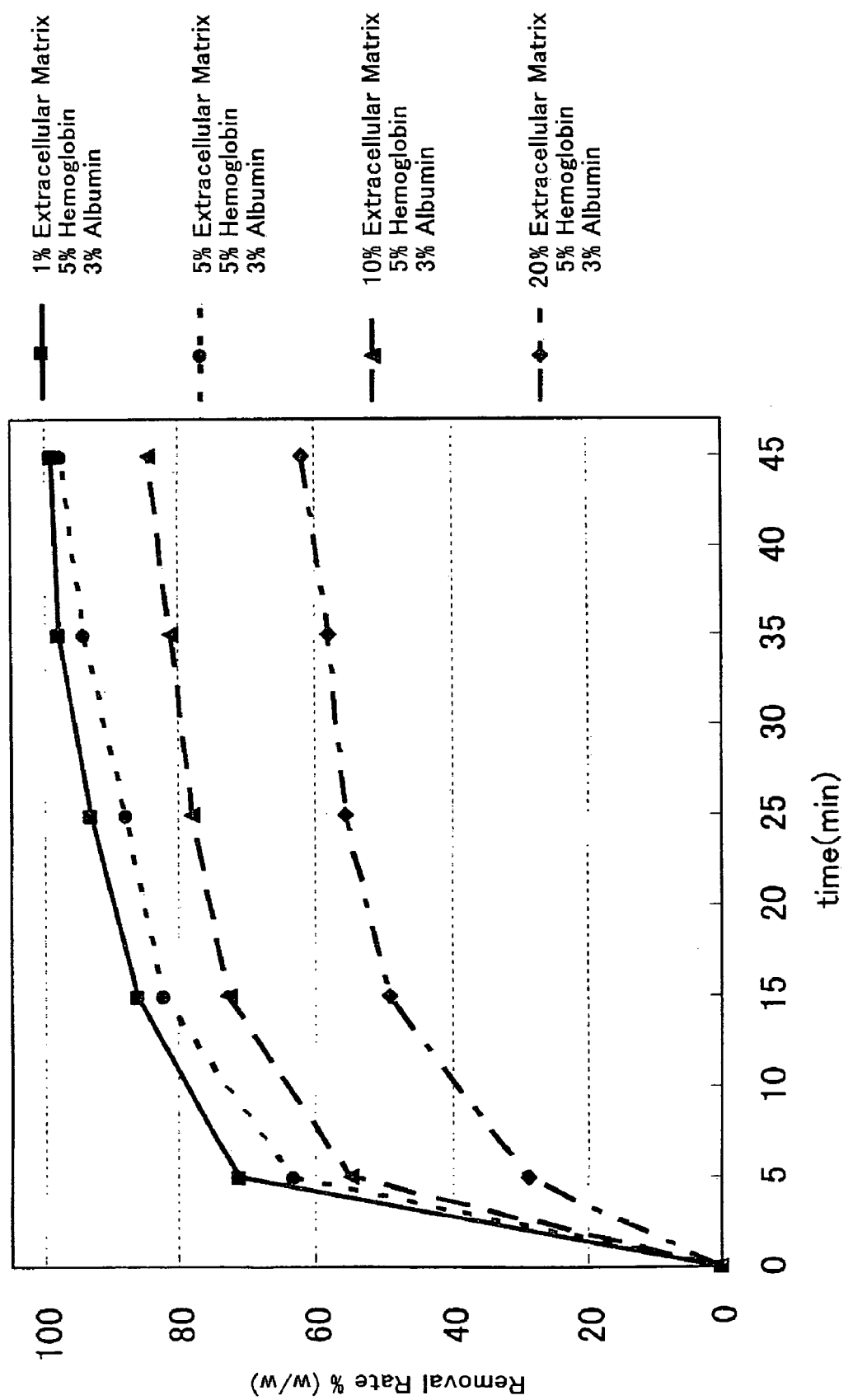
FIG. 3 is a graph which shows the time course of the removal rate of the contamination models when cleaning the indicator devices to which the indicator compositions, each having a different concentrations of the extracellular matrix component, had been applied.

As can be seen from FIG. 3, the degree of difficulty in cleaning varies depending on the concentration of the extracellular matrix component contained in the indicator compositions. The higher the concentration of the extracellular matrix component is, the harder to be cleaned the indicator composition is.

Therefore, according to the indicator composition of the present invention, it is possible to adjust the degree of difficulty in cleaning of the indicator composition applied onto the indicator device appropriately corresponding to the degree of contamination of a medical instrument to be cleaned.

This application relates to Japanese Patent Application No. 2005-192476 filed on Jun. 30, 2005.

The invention claimed is:

1. A method for evaluating the cleaning of a medical instrument comprising cleaning a medical instrument cleaning evaluation indicator device together with said medical instrument, wherein said indicator device is a test substrate on which an indicator composition comprising an extracellular matrix component and hemoglobin is applied, detecting a residual degree of said indicator composition remaining on said indicator device, and based on the result, determining the degree of cleaning of said medical instrument.

2. A method for setting cleaning conditions for medical instruments, comprising cleaning a medical instrument cleaning evaluation indicator device under predetermined cleaning conditions, wherein said indicator device is a test substrate on which an indicator composition comprising an extracellular matrix component and hemoglobin is applied, and detecting a residual degree of said indicator composition remaining on said indicator device after a predetermined time of the cleaning, and based on the results, setting cleaning conditions for medical instruments.

3. A method for checking a predetermined medical instrument cleaning process, comprising cleaning a medical instrument cleaning evaluation indicator device under said predetermined cleaning process, wherein said indicator device is a test substrate on which an indicator composition comprising an extracellular matrix component and hemoglobin is applied, and detecting a residual degree of said indicator composition remaining on said indicator device after a predetermined time of the cleaning, and based on the results, checking whether said cleaning process works properly.

4. The cleaning evaluation method according to claim 3, wherein the detection of the residual degree of said indicator composition is carried out by means of a color reaction of protein.

5. The cleaning evaluation method according to claim 4, wherein said color reaction of protein is a ninhydrin reaction.

6. A kit for evaluating the cleaning of a medical instrument, for setting cleaning conditions for medical instruments, and/or for checking a predetermined medical instrument cleaning process, comprising a combination of a medical instrument cleaning evaluation indicator device and a color reagent, wherein said indicator device is a test substrate on which an indicator composition comprising an extracellular matrix component and hemoglobin is applied.

7. The kit according to claim 6, wherein said extracellular matrix component is obtained from chicken cartilage.

8. The kit according to claim 6, wherein said extracellular matrix component comprises at least collagen and proteoglycan.

9. The kit according to claim 6, further comprising at least one component selected from the group consisting of serum protein, myoglobin, myosin, myosin filament, actin, actin filament, and lipid.

10. The kit according to claim 9, wherein said serum protein is albumin.

11. The kit according to claim 6, wherein a concentration of said extracellular matrix component in an aqueous suspension is from 0.1 to 50% by weight, and a concentration of said hemoglobin in an aqueous suspension is from 1 to 10% by weight.

12. The kit according to claim 6, wherein said indicator device is treated with a disinfectant.

* * * * *